(12) United States Patent
Sung et al.

(10) Patent No.: US 12,171,998 B2
(45) Date of Patent: Dec. 24, 2024

(54) QUALITY ASSURANCE APPARATUS AND METHOD FOR CANCER TREATMENT SYSTEM WITH ELECTRIC FIELD

(71) Applicant: FIELDCURE CO., LTD., Seoul (KR)

(72) Inventors: Hee Hun Sung, Seoul (KR); Jong Hyun Kim, Seoul (KR)

(73) Assignee: FIELDCURE CO., LTD., Seoul (KR)

( * ) Notice: Subject to any disclaimer, the term of this patent is extended or adjusted under 35 U.S.C. 154(b) by 291 days.

(21) Appl. No.: 17/799,894

(22) PCT Filed: Jul. 16, 2020

(86) PCT No.: PCT/KR2020/009403
§ 371 (c)(1),
(2) Date: Aug. 15, 2022

(87) PCT Pub. No.: WO2021/235592
PCT Pub. Date: Nov. 25, 2021

(65) Prior Publication Data
US 2023/0087717 A1  Mar. 23, 2023

(30) Foreign Application Priority Data
May 18, 2020  (KR) .......... 10-2020-0058964

(51) Int. Cl.
*A61N 1/36* (2006.01)
*A61N 1/04* (2006.01)

(52) U.S. Cl.
CPC ....... *A61N 1/0476* (2013.01); *A61N 1/36002* (2017.08)

(58) Field of Classification Search
CPC .. A61N 1/0476; A61N 1/36002; A61N 1/403; A61N 1/3603; A61N 1/40; A61N 1/08
See application file for complete search history.

(56) References Cited

U.S. PATENT DOCUMENTS

| 5,284,144 A | * | 2/1994 | Delannoy .......... G01R 33/4804 |
| | | | 977/911 |
| 5,540,737 A | * | 7/1996 | Fenn ........................ A61N 5/02 |
| | | | 607/101 |

(Continued)

FOREIGN PATENT DOCUMENTS

| EP | 2345451 | 7/2011 |
| KR | 10-1378875 | 3/2014 |

(Continued)

OTHER PUBLICATIONS

International Search Report mailed Feb. 2021 for PCT/KR2020/009403.

(Continued)

*Primary Examiner* — Ankit D Tejani
*Assistant Examiner* — Joshua Brendon Solomon (57) ABSTRACT

A quality assurance apparatus for a cancer treatment system with an electric field, comprising: an electric field generator configured to transmit an electric field to an inside of an electromagnetic phantom through an electrode array attached to the electromagnetic phantom; a measurement unit configured to measure any one of a voltage, a current, and an electric field inside the electromagnetic phantom; a data collection unit configured to collect a value measured by the measurement unit and convert the measured value into a digital value; an analysis unit configured to calculate and monitor a distribution and intensity of the electric field inside the electromagnetic phantom through the value transmitted from the data collection unit; and a verification unit configured to verify the electric field monitored by the analysis unit.

15 Claims, 5 Drawing Sheets

(56) References Cited

U.S. PATENT DOCUMENTS

| | | | |
|---|---|---|---|
| 2006/0199159 | A1 | 9/2006 | Ghiron et al. |
| 2010/0180702 | A1* | 7/2010 | Koyamashita ......... G09B 23/18 156/245 |
| 2010/0259259 | A1* | 10/2010 | Zahn .................. G01R 33/5601 324/309 |
| 2013/0001422 | A1* | 1/2013 | Lavon ..................... G01S 13/42 250/393 |
| 2017/0120041 | A1* | 5/2017 | Wenger .................... A61B 5/24 |
| 2017/0244110 | A1 | 8/2017 | Abdolahad et al. |
| 2017/0245928 | A1* | 8/2017 | Xiao ....................... H03K 3/017 |
| 2019/0314631 | A1* | 10/2019 | Wong ....................... A61N 1/40 |
| 2020/0330756 | A1* | 10/2020 | Schmidt ................... A61N 1/05 |

FOREIGN PATENT DOCUMENTS

| | | |
|---|---|---|
| KR | 10-1527939 | 6/2015 |
| KR | 10-2016-0073175 | 6/2016 |
| KR | 10-1688520 | 12/2016 |
| KR | 10-2017-0028601 | 3/2017 |
| KR | 10-2104961 | 4/2017 |
| KR | 10-2018-0072811 | 6/2018 |
| KR | 10-2018-0133431 | 12/2018 |
| KR | 10-2019-0022861 | 3/2019 |
| KR | 10-2019-0104036 | 9/2019 |
| KR | 10-2020-0008542 | 1/2020 |
| KR | 10-2020-0034588 | 3/2020 |

OTHER PUBLICATIONS

Ballo et al., "Correlation of Tumor Treating Fields Dosimetry to Survival Outcomes in Newly Diagnosed Glioblastoma: A Large-Scale Numerical Simulation-Based Analysis of Dara from the Phase 3 EF-14 Randomized Trial", Int J Radiation Oncol Biol Phys, vol. 104, No. 5, pp. 1106-1113, 2019.

Kirson et al., "Disruption of Cancer Cell Replication by Alternating Electric Fields", Cancer Research, vol. 64, 3288-3295, May 1, 2004.

Kirson et al., "Alternating Electric Fields Arrest Cell Proliferation in Animal Tumor Models and Human Brain Tumors", Proceedings of the National Academy of Science, vol. 104, No. 24, 10152-10157, Jun. 12, 2007.

* cited by examiner

QUALITY ASSURANCE APPARATUS AND METHOD FOR CANCER TREATMENT SYSTEM WITH ELECTRIC FIELD

This application claims the priority of Korean Patent Application No. 10-2020-0058964, filed on May 18, 2020 in the KIPO (Korean Intellectual Property Office), the disclosure of which is incorporated herein entirely by reference. Further, this application is the National Stage application of International Application No. PCT/KR2020/009403, filed on Jul. 16, 2020, which designates the United States and was published in Korean. Each of these applications is hereby incorporated by reference in their entirety into the present application.

TECHNICAL FIELD

The present invention relates to a quality assurance apparatus and method for a cancer treatment system with an electric field.

BACKGROUND ART

Techniques for treating cancer with electromagnetic waves involve treating cancer by removing tumors using different principles depending on treatment frequency bands. The principle used in an X-ray frequency band near 1010 MHz is to break and kill cancer cells' deoxyribonucleic acid (DNA) double helix, and another used in a 10 MHz frequency band is to remove cancer by generating heat within a tumor.

Techniques for treating cancer with an electric field (or tumor treating fields (TTFields)) were first reported in 2004 (see Non-Patent Documents 1 and 2), and involve treating cancer using the principle of delaying cell division and death by transmitting an AC electric field of low-intensity (1 to 3 V/cm) in an intermediate frequency band (50 to 500 kHz) to dividing tumor cells. Since a cancer treatment device with an electric field for patients with recurrent glioblastoma multiforme brain tumors was approved by the United States Food and Drug Administration (FDA) in 2011, despite its short history, as of 2020, it has received great interest and treatment is being performed at about 1,000 treatment centers worldwide.

Although it is known that the techniques for treating cancer with an electric field have little effect on normal cells, which divide very slowly compared to tumor cells, study results thereon are still insignificant and there is a potential risk of side effects that have not been shown yet. Therefore, it is necessary to transmit a minimal electric field to normal tissue in order to prevent side effects.

In order to effectively perform the technique, a treatment planning system (TPS) based on a patient's medical image using magnetic resonance imaging (MRI), computed tomography (CT), or the like is required. A general work procedure of a TPS is as follows. First, the patient's medical image (MRI, CT, etc.) is reconstructed into a three-dimensional medical image, boundaries of each tissue and tumor are segmented, and material constants required for electric field calculation, that is, electrical conductivity and dielectric constants (relative permittivity and relative dielectric constant), are assigned to each partitioned region. Thereafter, an insulated electrode array (or transducer array) is attached to the skin region and is subjected to mesh work, and then a voltage is calculated at each node and an electric field of each element is finally calculated, using a finite element method.

In Patent Document 3, which was previously filed by the present applicant, a method of transmitting an optimal result, that is, a method of transmitting a prescription electric field to a tumor and a minimum electric field to a normal tissue, by adjusting a position of each electrode and a magnitude of a current (or voltage) applied to the electrode using the above-described work procedure and an optimization algorithm is proposed.

However, a distribution and intensity of an electric field calculated by the TPS inevitably have a difference from a distribution and intensity of an electric field transmitted into a human body by a cancer treatment device with an electric field. In other words, an output error of the cancer treatment device with the electric field, an error due to an inaccurate position of the insulated electrode array, a modeling error that occurs in a process of converting medical image information into finite elements, a numerical analysis error of the finite element method, etc. are present.

Therefore, in order to verify the accuracy of distribution and intensity of the electric field, which are products of the TPS, there is a need for a technique for guaranteeing the quality of a cancer treatment system with an electric field.

(Patent Document 1) Korea University Industry-Academic Cooperation Foundation, "Method of treating cancer using fusion of alternative electric field and radiation therapy," Korean Patent Application Publication No. 10-2017-0028601, Published on Mar. 14, 2017.

(Patent Document 2) Korea University Industry-Academic Cooperation Foundation, "Method and apparatus for treating cancer using discontinuous fractional alternative electric field," Korean Patent Registration No. 10-1688520, published on Dec. 22, 2016.

(Patent Document 3) Korea University Industry-Academic Cooperation Foundation, FieldCure Co., Ltd., "Cancer electric field treatment apparatus using optimization algorithm," Korean Patent Registration No. 10-2104961, published on Apr. 27, 2020.

(Patent Document 4) BOMZON ZEEV, "Optimized TTField treatment of overhead electrode position based on MRI-based conductivity measurement," Korean Patent Application Publication No. 10-2018-0072811, published on Jun. 29, 2018.

(Patent Document 5) Novocure Limited, "Decreased motility of cancer cells using TTField," Korean Patent Application Publication No. 10-2018-0133431, published on Dec. 14, 2018.

(Patent Document 6) Novocure Limited, "Arrays for longitudinal transmission of tumor treating fields to body," Korean Patent Application Publication No. 10-2019-0022861, published on Mar. 6, 2019.

(Patent Document 7) BOMZON ZEEV, "Treatment of patients using tumor treating fields optimized with templates with variable electrode positions," Korean Patent Application Publication No. 10-2019-0104036, published on Sep. 5, 2019.

(Patent Document 8) Novocure Limited, "Temperature measurement in arrays to transmit tumor treating fields," Korean Patent Application Publication No. 10-2020-0008542, published on Jan. 28, 2020.

(Non-Patent Document 1) Kirson, Eilon D., et al., "Disruption of cancer cell replication by alternating electric fields," Cancer research 64.9 (2004): 3288-3295.

(Non-Patent Document 2) Kirson, Eilon D., et al., "alternating electric fields arrest cell proliferation in animal tumor models and human brain tumors," Proceedings of the National Academy of Sciences 104.24 (2007): 10152-10157.

(Non-Patent Document 3) Ballo, Matthew T., et al., "Correlation of tumor treating fields dosimetry to survival outcomes in newly diagnosed glioblastoma: A large-scale numerical simulation-based analysis of data from the phase 3 EF-14 randomized trial," International Journal of Radiation Oncology, Biology, Physics 104.5 (2019): 1106-1113.

DISCLOSURE OF THE INVENTION

Technical Problem

Therefore, there is a need in the art for a method of measuring and verifying a distribution and intensity of an electric field transmitted to a patient before or during treatment using an AC electric field for the purpose of cancer treatment with an electric field.

Objects of the present invention are not limited to the above-described object and other objects that are not described may be clearly understood by those skilled in the art from the following descriptions.

Technical Solution

According to an aspect of the present invention, there is provided a quality assurance apparatus for a cancer treatment system with an electric field.

The quality assurance apparatus for a cancer treatment system with an electric field may include an electric field generator configured to transmit an electric field to an inside of an electromagnetic phantom through an electrode array attached to the electromagnetic phantom, a measurement unit configured to measure any one of a voltage, a current, and an electric field inside the electromagnetic phantom, a data collection unit configured to collect a value measured by the measurement unit and convert the measured value into a digital value, an analysis unit configured to calculate and monitor a distribution and intensity of the electric field inside the electromagnetic phantom through the value transmitted from the data collection unit, and a verification unit configured to verify the electric field monitored by the analysis unit.

According to another aspect of the present invention, there is provided a quality assurance method for a cancer treatment system with an electric field.

The quality assurance method for a cancer treatment system with an electric field may include setting information on an electromagnetic phantom, a position of an electrode array, output information of an electric field generator, and a position of a probe array, calculating a distribution of an expected voltage and a distribution of an expected electric field of an inside of an electromagnetic phantom through a simulation on the basis of the set information, arranging the electrode array and the probe array in the electromagnetic phantom on the basis of the set information, applying, by an electromagnetic generator, an electric field to the inside of the electromagnetic phantom, measuring a distribution of a voltage and a distribution of an electric field inside the electromagnetic phantom through the probe array, determining whether a difference between the calculated distribution of the electric field and the measured distribution of the electric field is within a preset allowable range, and when it is determined that the difference is within the allowable range, determining that the cancer treatment system with an electric field is operating normally.

In addition, the solutions for solving the above-described objects do not enumerate all the characteristics of the present invention. Various features of the present invention and its advantages and effects may be understood in more detail with reference to the following specific embodiments.

Advantageous Effects

According to an embodiment of the present invention, by checking a distribution and intensity of an electric field transmitted to a patient before applying the electric field for the purpose of cancer treatment, to identify the accuracy of treatment, it is possible to prevent potential side effects and increase effectiveness of the treatment.

Effects of the present invention are not limited to the below-described effects and other effects that are not described may be clearly understood by those skilled in the art from the above detailed descriptions.

BEST MODE FOR CARRYING OUT THE INVENTION

Hereinafter, exemplary embodiments of the present invention that can be easily performed by those skilled in the art will be described in detail with reference to the accompanying drawings. However, in the description of the exemplary embodiments of the present invention, when it is determined that detailed descriptions of related well-known functions or configurations unnecessarily obscure the gist of the present invention, the detailed descriptions thereof will be omitted. Further, parts performing similar functions and operations throughout the drawings are denoted by the same reference numerals.

In addition, throughout this specification, when a part is referred to as being "connected" to another part, it includes "directly connected" and "indirectly connected" via an intervening part. Also, when a certain part "includes" a certain component, this does not exclude other components from being included unless described otherwise, and other components may in fact be included.

Generally, in a cancer treatment system with an electric field, an insulated electrode array is directly attached to a human body to form an electromagnetic field inside the human body and perform treatment, and in this case, it is not easy to directly measure an electric field formed inside the human body.

Therefore, in embodiments of the present invention that will be described below, an electromagnetic phantom which is formed in a structure similar to that of the human body using a biological material having material constants (e.g., electrical conductivity and dielectric constant) similar to those of the human body may be used. When a distribution of the electric field formed inside the electromagnetic phantom is measured by attaching electrodes to the electromagnetic phantom formed in this way, it is possible to identify a distribution of an electric field actually formed inside the human body.

Further, when a distribution of an electromagnetic field measured through the electromagnetic phantom matches a distribution of an electric field calculated by a simulation, it can be estimated that an intensity of the electric field calculated by the simulation is accurate.

Hereinafter, a quality assurance apparatus and method for a cancer treatment system with an electric field according to embodiments of the present invention will be described in more detail with reference to FIGS. 1 to 5.

Figure 1:
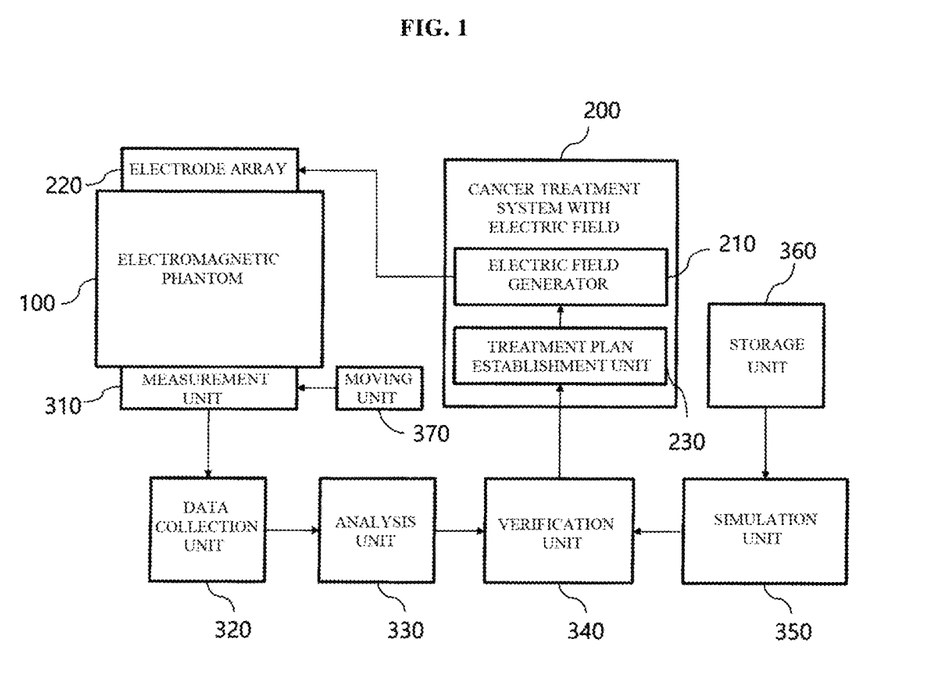
FIG. 1 is a configuration diagram of a quality assurance apparatus for a cancer treatment system with an electric field according to an embodiment of the present invention.

FIG. 1 is a configuration diagram of a quality assurance apparatus for a cancer treatment system with an electric field according to an embodiment of the present invention.

Referring to FIG. 1, the quality assurance apparatus for the cancer treatment system with the electric field according to the embodiment of the present invention may transmit an electric field to an inside of an electromagnetic phantom 100 to which an electrode array 220 is attached using an electric field generator 210 of a cancer treatment system 200 with an electric field, and may measure any one of a voltage, a current, and an electric field inside the electromagnetic phantom 100 through a measurement unit 310. Specifically, the measurement unit 310 may measure an impedance between electrodes, measure a current at one point, or directly measure the electric field, and may additionally measure temperatures at a plurality of points as necessary. Further, the measurement unit 310 may measure any one of the voltage, the current, and the electric field at each position while a position thereof is changed by a moving unit 370. Further, the measurement unit 310 may correct measured values using pre-stored calibration data.

A data collection unit 320 may collect the values measured by the measurement unit 310, convert the values into digital values, and transmit the converted digital values to an analysis unit 330.

The analysis unit 330 may calculate and monitor a distribution and intensity of the electric field inside the electromagnetic phantom 100 through the transmitted values. Specifically, the analysis unit 330 may monitor a distribution of the voltage, the distribution of the electric field, or a distribution of a square of the electric field inside the electromagnetic phantom 100 or monitor energy (product of permittivity and the square of the electric field) transmitted to a unit volume, and may additionally monitor a distribution of temperatures.

Meanwhile, a simulation unit 350 may calculate a distribution of an electric field to be formed inside the electromagnetic phantom 100 through a simulation using conductivity and permittivity of the electromagnetic phantom 100 stored in a storage unit 360, and a value of the electric field applied by the electric field generator 210.

A verification unit 340 may verify the electric field monitored by the analysis unit 330. Specifically, the verification unit 340 may comparatively analyze the distribution of the electric field calculated by the analysis unit 330 and the distribution of the electric field calculated by the simulation unit 350 to verify accuracy of the distribution of the electric field, and when a difference between the distributions of the electric fields is greater than or equal to a preset value, the verification unit 340 may dynamically change a treatment plan for treatment with an electric field, which is established by a treatment plan establishment unit 230. Further, the verification unit 340 may provide information on an error distribution up to a point at which the distributions of the electric fields calculated by the analysis unit 330 and the simulation unit 350 match.

Figure 2:
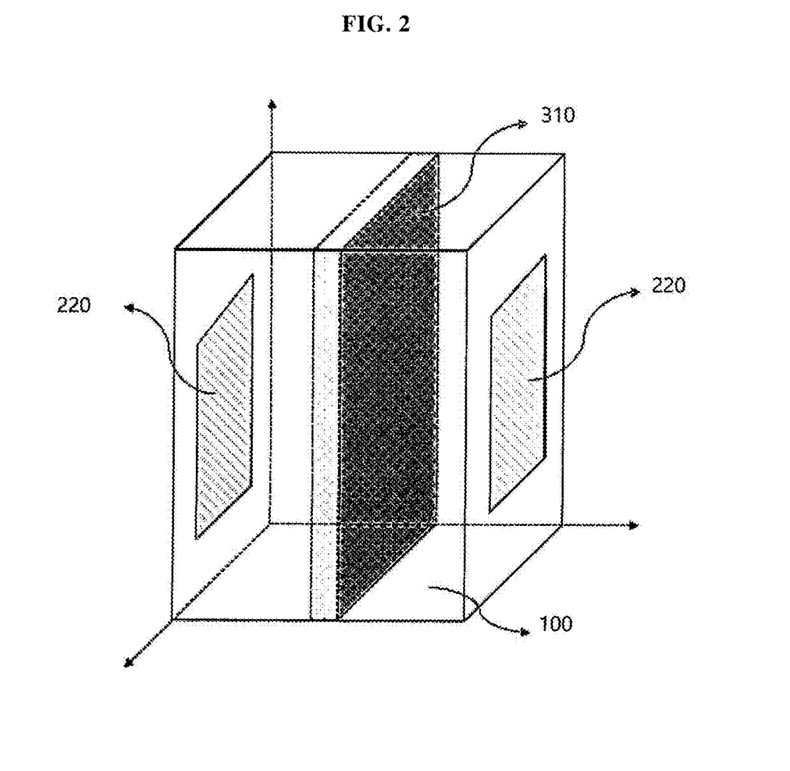
FIG. 2 is a diagram illustrating an electromagnetic phantom to which a plurality of electrode arrays is attached and a probe array for measuring a distribution and intensity of an electric field therein according to an embodiment of the present invention.
Figure 3:
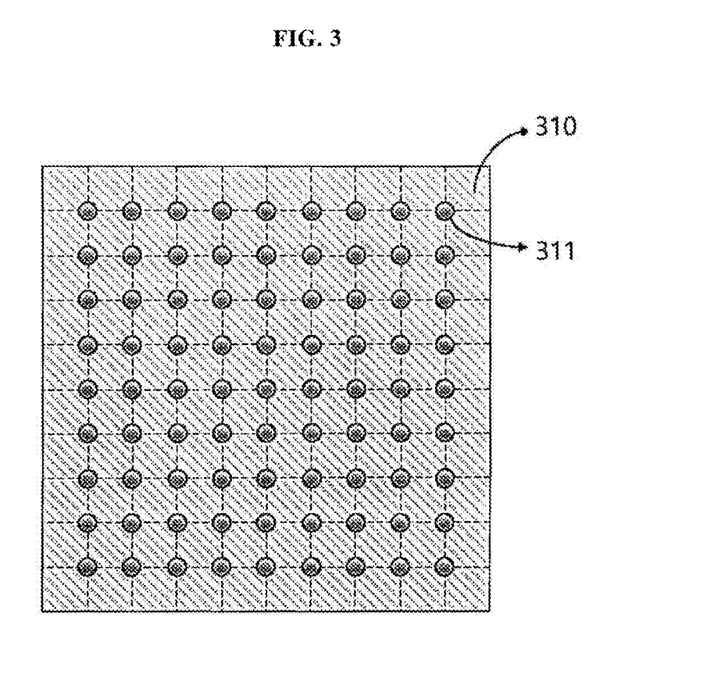
FIG. 3 is a diagram illustrating a probe array in which a plurality of probes is disposed according to an embodiment of the present invention.

FIG. 2 is a diagram illustrating an electromagnetic phantom to which a plurality of electrode arrays is attached and a probe array for measuring a distribution and intensity of an electric field therein according to an embodiment of the present invention, and FIG. 3 is a diagram illustrating a probe array in which a plurality of probes is disposed according to an embodiment of the present invention.

Referring to FIGS. 2 and 3, the electromagnetic phantom 100 used in the embodiment of the present invention may be made of a biological material having material constants, that is, electrical conductivity and dielectric constants, similar to those of the human body (i.e., a material whose material constants differ from those of the human body within preset ranges), and may be formed in a structure similar to that of the human body.

Here, a shape, a size, and material constants of the electromagnetic phantom 100 may be predetermined values, and the corresponding values may be stored in the storage unit 360 in order to perform an accurate simulation on the distribution and intensity of the electric field. Further, in consideration of the fact that the material constant is a frequency-dependent value, an AC impedance analyzer may be used to accurately determine the material constant.

In order to transmit an AC electric field to the inside of the electromagnetic phantom 100, one or more electrode arrays 220 are attached to an outside of the electromagnetic phantom 100, and the electric field generator 210 may flow an AC current of a preset treatment frequency (e.g., 50 to 500 kHz) or apply an AC voltage through one or more electrode arrays 220.

Accordingly, when the AC current flows through one or more electrode arrays 220, a voltage and an electric field may be generated inside the electromagnetic phantom 100, and a distribution of the generated electric field may be measured through the measurement unit 310, for example, implemented as a probe array.

According to an embodiment, as illustrated in FIG. 3, a probe array 310 may have a structure in which a plurality of probes 311 including probes for voltage measurement are arranged at preset intervals. Here, the current may be measured through each of the plurality of probes 311 or the electric field may be directly measured. Further, in order to rapidly and accurately measure the current or the electric field, a position of the probe array 310 may be automatically controlled by the moving unit 370 implemented as a stepping motor, a positioning device, or the like. Values measured by the plurality of probes 311 may be corrected using calibration data of each probe and may be converted into digital values together with corresponding position information by the data collection unit 320. Further, the analysis unit 330 may calculate and monitor a distribution of the electric field at each measurement position inside the electromagnetic phantom 100 using the digital values.

Figure 4:
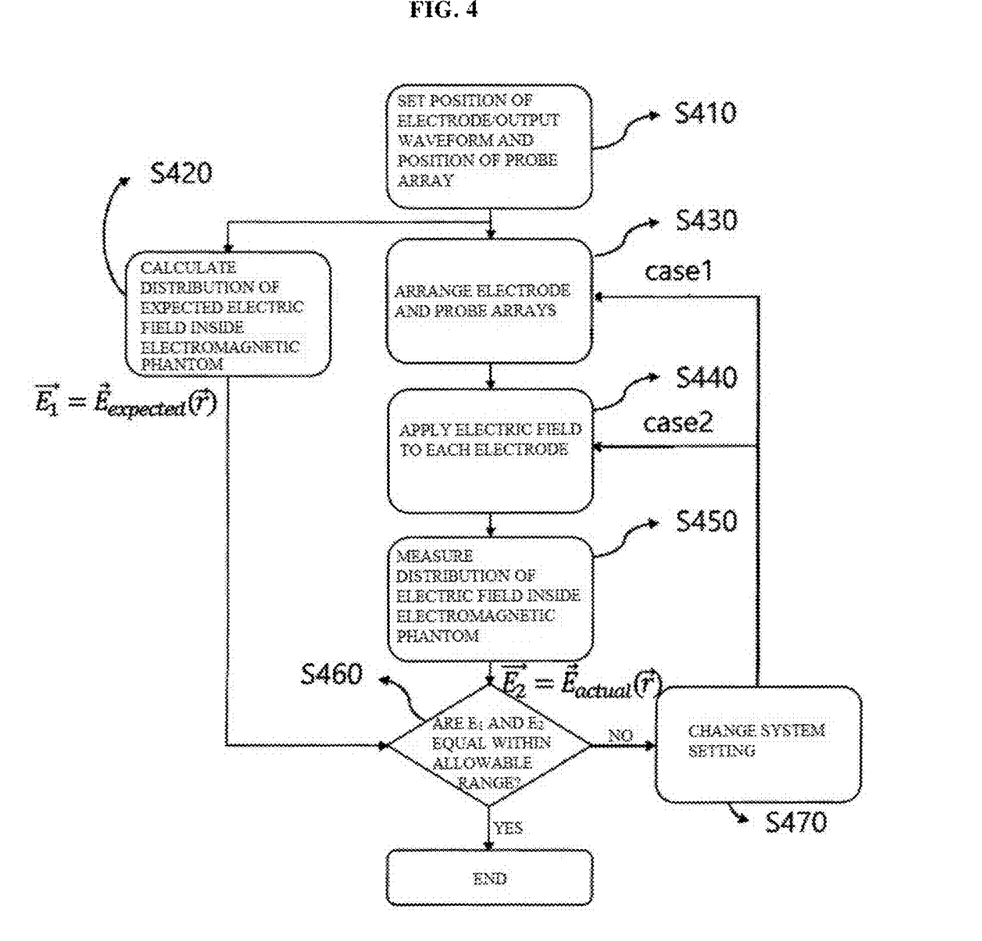
FIG. 4 is a flowchart of a quality assurance method for a cancer treatment system with an electric field according to another embodiment of the present invention.

FIG. 4 is a flowchart of a quality assurance method for a cancer treatment system with an electric field according to another embodiment of the present invention.

Referring to FIG. 4, first, in addition to information on the electromagnetic phantom (shape, size, and material constants of an electromagnetic phantom), which is used for electric field verification, a position of an electrode array, output information of the electric field generator (output waveform and intensity of a current from the electric field generator), a position of a probe array, and the like may be set (S410).

Thereafter, a distribution of an expected voltage and a distribution of an expected electric field inside the electromagnetic phantom may be calculated through a simulation on the basis of the information set in operation S410 (S420). The voltage and electric field calculated in this way are expressed as $V_{expected}$ and $E_{expected}$, respectively.

Thereafter, the electrode array and the probe array may be disposed in the electromagnetic phantom as set in operation S410 (S430), and the electric field may be applied to the inside of the electromagnetic phantom by flowing, by an electromagnetic generator, the current set in the electrode array (S440).

Thereafter, a distribution of a voltage and a distribution of an electric field inside the electromagnetic phantom may be measured through the probe array (S450). The voltage and electric field calculated in this way are expressed as $V_{actual}$ and $E_{actual}$, respectively.

Thereafter, it is determined whether a difference between the distributions of two electric fields is within a preset allowable range (S460), and when it is determined that the difference is within the corresponding range, it may be determined that the cancer treatment system with the electric field is operating normally and the method may be completed.

In this case, various comparison indices such as the Euclidean distance (or $L^2$ norm) of Equation 1 or a percentage error of Equation 2 may be used to compare the distributions of two electric fields. Here, various indices such as those in Equations 3 to 7 may be used for x. In Equation 5, $\varepsilon$ denotes vacuum permittivity, and $E_r$ denotes relative permittivity of a tumor. In Equations 6 and 7, $\sigma$ denotes electrical conductivity of the tumor. Equation 5 and Equation 6 represent stored energy and consumed energy per unit volume of the tumor, respectively. Equation 7 represents a power loss density per unit volume of the tumor.

$$L^2_{norm} = \|x_{actual} - x_{expected}\|_2 = \sqrt{\sum_{i=1}^{n} |x_{actual}[i] - x_{expected}[i]|^2} \quad \text{[Equation 1]}$$

$$\text{percentage error} = \frac{\|x_{actual} - x_{expected}\|_2}{\|x_{actual}\|_2} \times 100\% \quad \text{[Equation 2]}$$

$$x = V(x, y, z) \quad \text{[Equation 3]}$$

$$x = \vec{E}(x, y, z) \quad \text{[Equation 4]}$$

$$x = \frac{1}{2}\varepsilon\varepsilon_r |\vec{E}(x, y, z)|^2 \quad \text{[Equation 5]}$$

$$x = \frac{1}{2}\frac{\sigma}{\omega}|\vec{E}(x, y, z)|^2 \quad \text{[Equation 6]}$$

$$x = \frac{1}{2}\sigma|\vec{E}(x, y, z)|^2 \quad \text{[Equation 7]}$$

The most important indicator in radiation therapy is a dose irradiated to a tumor and normal organs. Here, the dose is the unit (Gy=J/kg) of energy per unit mass. Similarly, in the cancer treatment with the electric field, a treatment electric field transmitted to a tumor and normal cells may be expressed as energy per unit volume as in Equations 5 and 6 described above. Meanwhile, in Non-Patent Document 3, the power loss density as shown in Equation 7 is proposed as a dose density of a technique for treating cancer with an electric field.

Further, in the radiation therapy, treatment is performed through energy of radiation absorbed by a patient. Even in the cancer treatment with the electric field, when the difference between the distributions is out of the above-described allowable range, causes of several errors may be considered to check a value of energy transmitted to the patient.

As an example, when the position of the electrode array or probe array is not a planned position (case 1), the corresponding position may be checked and the electrode array or the probe array may be rearranged (S430), and operations S440 to S460 may be performed again.

As another example, when a setting error of the electric field generator or a functional error of hardware is generated (case 2), the setting of the electromagnetic generator may be checked and changed (S470), and then operations S440 to S460 may be performed again.

Figure 5:
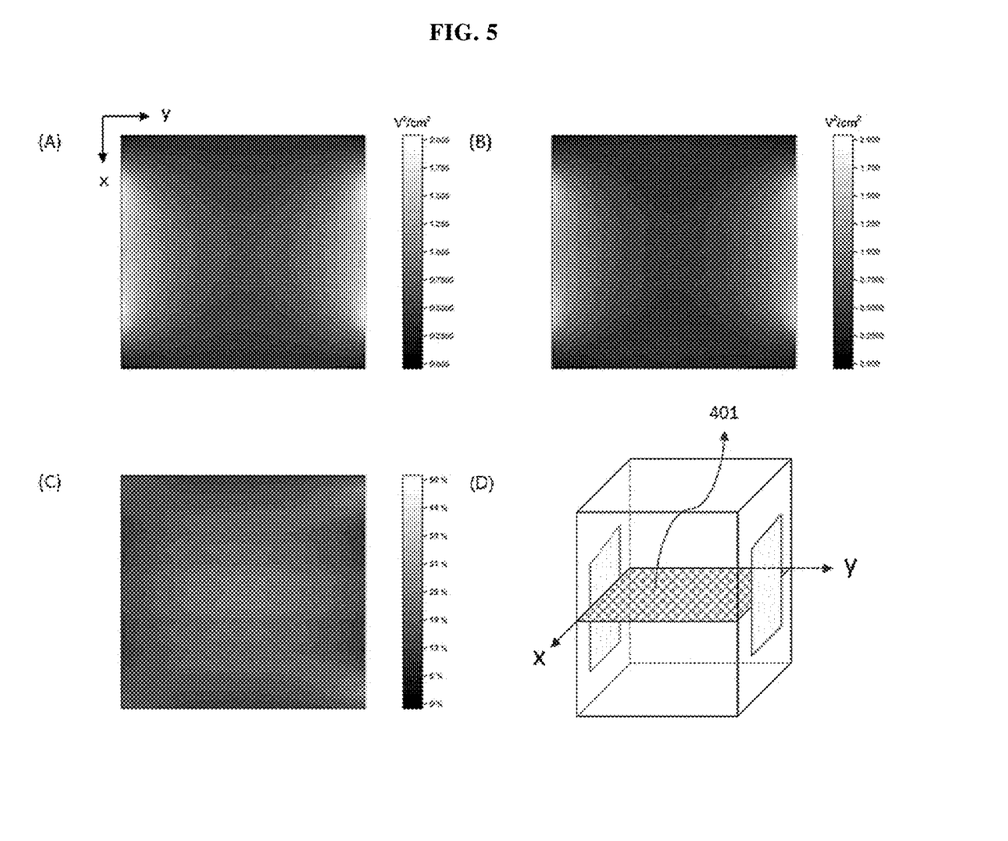
FIG. 5 shows diagrams showing a distribution of a square of an expected electric field and a distribution of a square of a measured electric field according to an embodiment of the present invention.

FIG. 5 is a diagram illustrating a distribution of an expected voltage and a distribution of a measured voltage according to an embodiment of the present invention, and illustrates a result of comparing a distribution $|\vec{E}_{expected}|^2$ in (A) of FIG. 5 calculated by a simulation and a distribution $|\vec{E}_{actual}|^2$ in (B) of FIG. 5 measured on a horizontal plane 401 between two electrodes, when two flat electrode arrays (10×10 cm$^2$) are attached to a box-shaped electromagnetic phantom (20×20×20 cm$^3$) filled with water (electrical conductivity $\sigma$=0.02 S/m and relative permittivity $\varepsilon_r$=81), and the electric field generator flows an AC current of 200 kHz. Here, the probes are disposed every 1 cm along each of an X-axis and a Y-axis. Further, (C) of FIG. 5 shows percent errors of two distributions. It can be seen that an average of the percent error for $|\vec{E}|^2$ is 18.0±3.1%, which is greater than an average of the percent error for $|\vec{E}|$ of 9.5±1.7%.

The present invention is not limited by the above-described embodiments and the accompanying drawings. It will be apparent to those of ordinary skill in the art that the components according to the present invention can be substituted, modified, and changed without departing from the spirit of the present invention.

The invention claimed is:

1. A quality assurance apparatus for a cancer treatment system with an electric field, the quality assurance apparatus comprising:
    an electric field generator configured to transmit an electric field to an inside of a physical electromagnetic phantom through an electrode array attached to the physical electromagnetic phantom;
    a measurement unit configured to measure any one of a voltage, a current, and an electric field inside the physical electromagnetic phantom;
    a data collection unit configured to collect a value measured by the measurement unit and convert the measured value into a digital value;
    an analysis unit configured to calculate and monitor a distribution and intensity of the electric field inside the physical electromagnetic phantom through the value transmitted from the data collection unit; and
    a verification unit configured to verify the electric field monitored by the analysis unit.

2. The quality assurance apparatus of claim 1, wherein the electric field generator generates an electric field of 50 to 500 kHz.

3. The quality assurance apparatus of claim 1, wherein the measurement unit measures an impedance between electrodes included in the electrode array.

4. The quality assurance apparatus of claim 1, wherein the measurement unit measures a current at one point of the physical electromagnetic phantom.

5. The quality assurance apparatus of claim 1, wherein the measurement unit measures an electric field of the physical electromagnetic phantom.

6. The quality assurance apparatus of claim 1, further comprising a moving unit configured to move a position of the measurement unit,
wherein the measurement unit measures any one of a voltage, a current, and an electric field at each position to which the measurement unit is moved by the moving unit.

7. The quality assurance apparatus of claim 1, wherein the measurement unit corrects the measured value using pre-stored calibration data.

8. The quality assurance apparatus of claim 1, wherein the analysis unit monitors a distribution of a voltage, a distribution of an electric field, and a distribution of a square of the electric field inside the physical electromagnetic phantom, or monitors energy transmitted to a unit volume.

9. The quality assurance apparatus of claim 1, wherein:
the measurement unit further measures temperatures at a plurality of points of the physical electromagnetic phantom; and
the analysis unit further monitors a distribution of the temperatures of the physical electromagnetic phantom.

10. The quality assurance apparatus of claim 1, further comprising a simulation unit configured to calculate a distribution of the electric field to be formed inside the physical electromagnetic phantom through a simulation using conductivity and permittivity of the physical electromagnetic phantom and a value of the electric field applied by the electric field generator.

11. The quality assurance apparatus of claim 10, wherein the verification unit comparatively analyzes the distribution of the electric field calculated by the analysis unit and the distribution of the electric field calculated by the simulation unit, and when a difference between the distributions of the electric fields is greater than or equal to a preset value, dynamically changes a treatment plan for cancer treatment with the electric field.

12. The quality assurance apparatus of claim 1, wherein the physical electromagnetic phantom is made of a material whose material constant differs within a preset range from that of a human body.

13. A quality assurance method for a cancer treatment system with an electric field, the quality assurance method comprising:
setting information on a physical electromagnetic phantom, a position of an electrode array, output information of an electric field generator, and a position of a probe array;
calculating a distribution of an expected voltage and a distribution of an expected electric field of an inside of the physical electromagnetic phantom through a simulation on the basis of the set information;
arranging the electrode array and the probe array in the physical electromagnetic phantom on the basis of the set information;
applying, by an electromagnetic generator, an electric field to the inside of the physical electromagnetic phantom;
measuring a distribution of a voltage and a distribution of an electric field inside the physical electromagnetic phantom through the probe array;
determining whether a difference between the calculated distribution of the electric field and the measured distribution of the electric field is within a preset allowable range; and
when it is determined that the difference is within the allowable range, determining that the cancer treatment system with an electric field is operating normally.

14. The quality assurance method of claim 13, wherein, when it is determined that the difference is out of the allowable range, the position of the electrode array or probe array is identified and the electrode array or probe array is rearranged, and then the applying of the electric field, the measuring of the distribution of the electric field, and the determining of whether the difference is within the allowable range are performed again.

15. The quality assurance method of claim 13, wherein, when it is determined that the difference is out of the allowable range, the setting of the electromagnetic generator is identified and changed, and then the applying of the electric field, the measuring of the distribution of the electric field, and the determining of whether the difference is within the allowable range are performed again.

* * * * *